(12) United States Patent
Tripathi et al.

(10) Patent No.: US 11,908,551 B2
(45) Date of Patent: Feb. 20, 2024

(54) SYSTEM AND METHOD FOR IDENTIFYING POTENTIAL TARGETS FOR PHARMACEUTICAL COMPOUND

(71) Applicant: Innoplexus AG, Eschborn (DE)

(72) Inventors: Gaurav Tripathi, Pune (IN); Om Sharma, Dhanbad (IN); Vatsal Agarwal, Rampur (IN); Anurag Chandrekar, Raipur (IN)

(73) Assignee: INNOPLEXUS AG, Eschborn (DE)

( * ) Notice: Subject to any disclaimer, the term of this patent is extended or adjusted under 35 U.S.C. 154(b) by 1365 days.

(21) Appl. No.: 16/366,142

(22) Filed: Mar. 27, 2019

(65) Prior Publication Data

US 2020/0090789 A1 Mar. 19, 2020

(30) Foreign Application Priority Data

Mar. 27, 2018 (GB) ...................................... 1804870

(51) Int. Cl.
| | |
|---|---|
| *G16C 20/50* | (2019.01) |
| *G16B 15/30* | (2019.01) |
| *G16C 20/60* | (2019.01) |
| *G16B 5/00* | (2019.01) |
| *G16B 50/30* | (2019.01) |
| *G16C 20/30* | (2019.01) |
| *G16C 20/90* | (2019.01) |
| *G16C 20/70* | (2019.01) |

(52) U.S. Cl.
CPC .............. *G16C 20/50* (2019.02); *G16B 5/00* (2019.02); *G16B 50/30* (2019.02); *G16C 20/30* (2019.02); *G16C 20/60* (2019.02); *G16C 20/70* (2019.02); *G16C 20/90* (2019.02)

(58) Field of Classification Search
CPC ........ G16C 20/50; G16C 20/30; G16C 20/60; G16C 20/70; G16C 20/90; G16B 5/00; G16B 50/30; G16B 15/30; G16B 20/20; G16B 40/00; G16B 99/00
See application file for complete search history.

(56) References Cited

PUBLICATIONS

Koscielny et al., Open Target: A Platform for Therapeutic Target Identification and Validation, Published Online Dec. 8, 2016, Nucleic Acids Research, vol. 45, Database Issue, pp. D985-D994 (Year: 2016).*

* cited by examiner

*Primary Examiner* — Toan M Le
(74) *Attorney, Agent, or Firm* — ZIEGLER IP LAW GROUP, LLC

(57) ABSTRACT

A system and method for identifying potential targets for a pharmaceutical compound. The system includes a database arrangement operable to store existing data sources and information related to the pharmaceutical compound; and a processing module communicably coupled to database arrangement. The processing module is operable to receive information related to the pharmaceutical compound, wherein the information includes at least one known target associated with the pharmaceutical compound; extract plurality of targets from existing data sources, wherein the existing data sources comprise plurality of data records and wherein each of the plurality of targets is associated with the pharmaceutical compound in at least one data record; analyse druggability of each of plurality of targets to determine a preliminary set of targets; determine net score for each of the targets in preliminary set of targets; and designate targets with a net score above a predefined threshold, as potential targets.

11 Claims, 2 Drawing Sheets

SYSTEM AND METHOD FOR IDENTIFYING POTENTIAL TARGETS FOR PHARMACEUTICAL COMPOUND

CROSS-REFERENCE TO RELATED APPLICATIONS

This application claims the benefit under 35 U.S.C. § 119(a) and 37 CFR § 1.55 to UK Patent Application No. GB1804870.2, filed on Mar. 27, 2018, the entire content of which is incorporated herein by reference.

TECHNICAL FIELD

The present disclosure relates generally to data mining and processing; and more specifically, to systems that identifies potential targets for pharmaceutical compounds. Furthermore, the present disclosure relates to methods for identifying potential targets for pharmaceutical compounds. Moreover, the present disclosure also relates to computer readable medium containing program instructions for execution on a computer system, which when executed by a computer, cause the computer to perform method steps of identifying potential targets for a pharmaceutical compound.

BACKGROUND

In recent years, increased population and pollution have led to an unprecedented growth of diseases across the globe. In order to overcome the array of challenges, drug discoveries are advancing rapidly, researches and experiments are also going on a regular basis. Furthermore, World Health Organisation (WHO) and Food and Drug Administration (FDA) have taken major steps to enhance the drug development globally. Generally, a pharmaceutical compound (namely, drug) taken in account for development, undergoes multiple cycles of clinical trials, laboratory tests and so forth, before being introduced for public use. Consequently, development of a pharmaceutical compound is a lengthy and expensive process and consumes an average of fifteen years. Therefore, drug repositioning is taken in practice to reduce the cost and duration of drug development and find alternative uses of known and approved pharmaceutical compounds.

Generally, drug repositioning relates to utilizing a known pharmaceutical compound to cure an alternative disease and reduce tests and trials associated with development of a new pharmaceutical compound. Conventionally, alternative uses for a known pharmaceutical compound were mostly performed by hit-and-trial approaches. Recently, systematic approaches have been taken into account for drug repositioning to obtain a better and effective set of results. Firstly, a target-based approach is employed for drug repositioning. In such an instance, structural similarity of known and potential targets for a pharmaceutical compound is analysed. Moreover, computational methods employed for drug repurposing are being developed involving prediction of potential targets using data analysis. Furthermore, drug development organisations have an account of data associated with the relations between drugs and diseases that are recognised across the world. However, the drug development organisations have not succeeded in meeting the appropriate curriculum of widespread accessibility of such data. Additionally, the data provided are not sufficient in combining the relations to establish an alternative drug for the same disease, or to cure an alternate disease with a recognised drug. However, conventional methods for drug repositioning do not provide a validated and approved set of results for known pharmaceutical compounds.

Therefore, in light of the foregoing discussion, there exists a need to overcome the drawbacks associated with conventional methods of drug repositioning.

SUMMARY

The present disclosure seeks to provide a system that identifies potential targets for a pharmaceutical compound. The present disclosure also seeks to provide a method of identifying potential targets for a pharmaceutical compound. The present disclosure also seeks to provide a computer readable medium containing program instructions for execution on a computer system, which when executed by a computer, cause the computer to perform method steps for method of identifying potential targets for a pharmaceutical compound. The present disclosure seeks to provide a solution to the existing problem of ineffective and speculative potential targets provided by conventional methods of drug repositioning. An aim of the present disclosure is to provide a solution that overcomes at least partially the problems encountered in prior art, and provides an efficient and reliable method of identifying potential targets for a pharmaceutical compound.

In one aspect, an embodiment of the present disclosure provides a system that identifies potential targets for a pharmaceutical compound, wherein the system includes a computer system, wherein the system comprises:
  a database arrangement operable to store existing data sources and information related to the pharmaceutical compound; and
  a processing module communicably coupled to the database arrangement, the processing module operable to:
    receive information related to the pharmaceutical compound, wherein the information comprises at least one known target associated with the pharmaceutical compound;
    extract plurality of targets from existing data sources, wherein the existing data sources comprise plurality of data records and wherein each of the plurality of targets is associated with the pharmaceutical compound in at least one data record;
    analyse druggability of each of the plurality of targets to determine a preliminary set of targets;
    determine a net score for each of the targets in the preliminary set of targets; and
    designate targets with a net score above a predefined threshold, as the potential targets.

In another aspect, an embodiment of the present disclosure provides a method of identifying potential targets for a pharmaceutical compound, wherein the method includes using a computer system, wherein the method comprises:
  specifying the pharmaceutical compound, wherein the pharmaceutical compound is associated with at least one known target;
  extracting plurality of targets from existing data sources, wherein the existing data sources comprise plurality of data records and wherein each of the plurality of targets is associated with the pharmaceutical compound in at least one data record;
  analysing druggability of each of the plurality of targets to determine a preliminary set of targets;
  determining a net score for each of the targets in the preliminary set of targets; and
  designating targets with a net score above a predefined threshold, as the potential targets.

In yet another aspect, an embodiment of the present disclosure provides a computer readable medium containing program instructions for execution on a computer system, which when executed by a computer, cause the computer to perform method steps for method of identifying potential targets for a pharmaceutical compound, the method comprising the steps of:
specifying the pharmaceutical compound, wherein the pharmaceutical compound is associated with at least one known target;
extracting plurality of targets from existing data sources, wherein the existing data sources comprise plurality of data records and wherein each of the plurality of targets is associated with the pharmaceutical compound in at least one data record;
analysing druggability of each of the plurality of targets to determine a preliminary set of targets;
determining a net score for each of the targets in the preliminary set of targets; and
designating targets with a net score above a predefined threshold, as the potential targets.

Embodiments of the present disclosure substantially eliminate or at least partially address the aforementioned problems in the prior art, and enables provides a reliable and validated set of potential targets for a pharmaceutical compound.

Additional aspects, advantages, features and objects of the present disclosure would be made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those in the art will understand that the drawings are not to scale. Wherever possible, like elements have been indicated by identical numbers.

Embodiments of the present disclosure will now be described, by way of example only, with reference to the following diagrams wherein.

Figure 1:
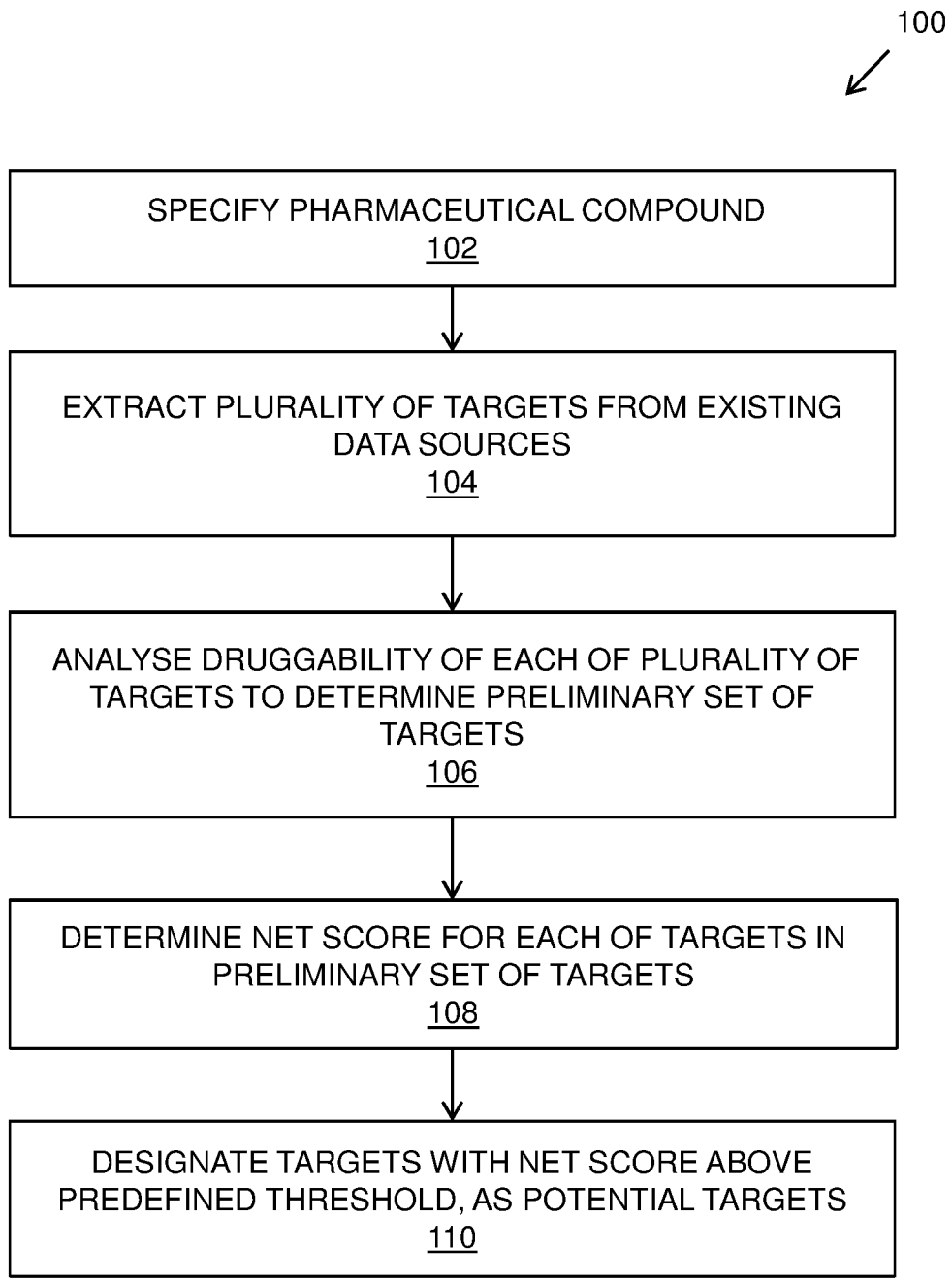
FIG. 1 is an illustration of steps of a method of identifying potential targets for a pharmaceutical compound, in accordance with an embodiment of the present disclosure.

In the accompanying drawings, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DETAILED DESCRIPTION OF EMBODIMENTS

In overview, embodiments of the present disclosure are concerned with identifying potential targets for a pharmaceutical compound and specifically to, analysing existing data to provide validated unidentified targets for pharmaceutical compounds.

The following detailed description illustrates embodiments of the present disclosure and ways in which they can be implemented. Although some modes of carrying out the present disclosure have been disclosed, those skilled in the art would recognize that other embodiments for carrying out or practicing the present disclosure are also possible.

In one aspect, an embodiment of the present disclosure provides a system that identifies potential targets for a pharmaceutical compound, wherein the system includes a computer system, wherein the system comprises:
a database arrangement operable to store existing data sources and information related to the pharmaceutical compound; and
a processing module communicably coupled to the database arrangement, the processing module operable to:
receive information related to the pharmaceutical compound, wherein the information comprises at least one known target associated with the pharmaceutical compound;
extract plurality of targets from existing data sources, wherein the existing data sources comprise plurality of data records and wherein each of the plurality of targets is associated with the pharmaceutical compound in at least one data record;
analyse druggability of each of the plurality of targets to determine a preliminary set of targets;
determine a net score for each of the targets in the preliminary set of targets; and
designate targets with a net score above a predefined threshold, as the potential targets.

In another aspect, an embodiment of the present disclosure provides a method of identifying potential targets for a pharmaceutical compound, wherein the method includes using a computer system, wherein the method comprises:
specifying the pharmaceutical compound, wherein the pharmaceutical compound is associated with at least one known target;
extracting plurality of targets from existing data sources, wherein the existing data sources comprise plurality of data records and wherein each of the plurality of targets is associated with the pharmaceutical compound in at least one data record;
analysing druggability of each of the plurality of targets to determine a preliminary set of targets;
determining a net score for each of the targets in the preliminary set of targets; and
designating targets with a net score above a predefined threshold, as the potential targets.

The present disclosure provides a reliable and efficient system and method for identifying potential targets for a pharmaceutical compound. Beneficially, the method described in the present disclosure accounts for multiple parameters such as druggability of a potential target, mutations in the target and so forth to provide an accurate prediction of potential targets for a pharmaceutical compound.

Furthermore, the set of potential targets provided by the method of the present disclosure have a high probability of success in subsequent laboratory tests. Additionally, the method is straightforward and easy-to-implement. Moreover, the method takes into account a diversity of targets to identify a comprehensive set of potential targets for a pharmaceutical compound.

The computer system relates to at least one computing unit comprising a central storage system, processing units and various peripheral devices. Optionally, the computer system relates to an arrangement of interconnected computing units, wherein each computing unit in the computer system operates independently and may communicate with other external devices and other computing units in the computer system.

The term "system that identifies" is used interchangeably with the term "system for identifying", wherever appropriate i.e. whenever one such term is used it also encompasses the other term.

Throughout the present disclosure, the term "pharmaceutical compound" relates to a medicament, medication, medicine, pharmaceutical, drug, and so forth used for healing, treating, altering, improving, restoring, relieving, and/or curing a particular condition, disease, or mental or physical state, which includes the active ingredient or combination of active ingredients and inactive ingredients infused into an expedient or dissolved in some other carrier. Additionally, the pharmaceutical compound is approved for public use thereof by an approved regulatory government agency.

Throughout the present disclosure, the term "targets" relates to biological sites within a living organism, where the pharmaceutical compound binds, thereby resulting in a change in behaviour or function of the target. Moreover, the targets may comprise proteins, nucleic acids and so forth. Furthermore, the targets may be native protein in the body whose activity is regulated on binding with the pharmaceutical compound. In addition, the pharmaceutical compound binds with the target to cure a disease and achieve therapeutic effect. Specifically, the pharmaceutical compound enacts on the potential target providing a therapeutic effect, the pharmaceutical compound is compatible of providing the therapeutic effect to the aforesaid target. In an example, the target may be a site where virus of a disease attacks and results in malfunctioning of the target. Furthermore, a pharmaceutical compound is associated with at least one known target. Specifically, the pharmaceutical compound is known to provide therapeutic effect at such at least one known target. Additionally, the pharmaceutical compound may comprise unidentified sites of action, wherein the pharmaceutical compound may have a therapeutic effect on such unidentified sites of action. Such unidentified sites of action are termed as "potential targets". Furthermore, the therapeutic effect of the pharmaceutical compound at such unidentified sites of action is not widely known in the public or scientific community.

Throughout the present disclosure, the term "database arrangement" relates to an organized body of digital data regardless of the manner in which the data or the organized body thereof is represented. Optionally, the database arrangement may be hardware, software, firmware and/or any combination thereof. For example, the organized body of related data may be in the form of a table, a map, a grid, a packet, a datagram, a file, a document, a list or in any other form. The database arrangement includes any data storage software and systems, such as, for example, a relational database like IBM DB2 and Oracle 9. Furthermore, the database arrangement may include to the software program for creating and managing one or more databases. Optionally, the database arrangement may be operable to support relational operations, regardless of whether it enforces strict adherence to the relational model, as understood by those of ordinary skill in the art. Additionally, the database arrangement may be populated by digital data (namely, data elements). Furthermore, the database arrangement is operable to store the information related to the pharmaceutical compound. Specifically, the information related to the pharmaceutical compound comprises, but not limited to, known targets of the pharmaceutical compound, chemical composition, clinical trials data related to the pharmaceutical compound.

The method of identifying potential targets for the pharmaceutical compound comprises specifying the pharmaceutical compound. The system for identifying potential targets for the pharmaceutical compound comprises a database arrangement operable to store information related to the pharmaceutical compound. It will be appreciated that the information of the known target includes a recognized structure, identified and defined family, described mechanisms and so forth related therewith.

Optionally, the pharmaceutical compound is specified based on a user-input. Specifically, a user may specify the pharmaceutical compound. More specifically, the user may provide the input using the processing module. Furthermore, the input may comprise selecting the pharmaceutical compound from a list of pharmaceutical compounds stored in the database arrangement. Consequently, the processing module is operable to receive information related to the pharmaceutical compound specified by the user.

Optionally, the pharmaceutical compound is specified by the processing module. Specifically, the processing module is operable to specify the pharmaceutical compound by selecting from a list of pharmaceutical compounds stored in the database arrangement. Furthermore, the processing module may be operable to select pharmaceutical compound sequentially from the list to identify potential targets for each of the pharmaceutical compound in the list. Consequently, the processing module is operable to receive information related to the pharmaceutical compound selected thereby.

Throughout the present disclosure, the term "processing module" herein relates to a processing device that is operable to receive information related to the pharmaceutical compound. Optionally, the processing module includes, but is not limited to, a microprocessor, a microcontroller, a complex instruction set computing (CISC) microprocessor, a reduced instruction set (RISC) microprocessor, a very long instruction word (VLIW) microprocessor, or any other type of processing circuit. Furthermore, the term 'processing module' may refer to one or more individual processors, processing devices and various elements associated with the processing device that may be shared by other processing devices. Additionally, the one or more individual processors, processing devices and elements are arranged in various architectures for responding to and processing the instructions that drive the system. Furthermore, the processing module is communicably coupled to the database arrangement, the processing module is operable to receive information related to the pharmaceutical compound. Optionally, the processing module is communicably coupled to the database arrangement via a communication channel (wired or wireless).

Throughout the present disclosure, the term "existing data sources" relates to organized or unorganized bodies of digital information regardless of manner in which data is represented therein. The existing data sources may be hardware, software, firmware and/or any combination thereof. For example, the existing data sources may be in form of tables, maps, grids, packets, datagrams, files, documents, lists or in any other form. The existing data sources include any data storage software and systems, such as, for example, a relational database like IBM, DB2, Oracle 9 and so forth. Moreover, the existing data sources may include the data in form of text, audio, video, image and/or a combination thereof. Furthermore, the existing data sources may comprise, but not limited to, databases of drug regulatory authorities of various jurisdictions such as NCBI (National Centre for Biotechnology Information), FDA (Food and Drug Administration), and so forth. Furthermore, existing data sources may include chemical and drug-target databases, such as Therapeutic Targets Database (TTD), DrugBank, Binding DB, including information related to biological targets. Furthermore, the existing data sources may include data from various publications, research organizations, pharmaceutical organizations, and so forth. The existing data sources comprise plurality of data records. Furthermore, the term 'data-records' refers to the information related to the pharmaceutical compounds. Furthermore, the information in the data-records may include data in form of, but not limited to, articles, research papers, publication, dissertations, files, documents relating to pharmaceutical compounds and targets.

The method of identifying potential targets for the pharmaceutical compound comprises extracting plurality of targets from the existing data sources. Furthermore, the processing module operable to extract plurality of targets from the existing data sources. Specifically, the processing module is operable to crawl existing data sources to identify data records associating the specified pharmaceutical compound with targets. More specifically, a plurality of targets are identified from the existing sources, wherein each of the plurality of targets is associated with the specified pharmaceutical compound in at least one data record, and extracted thereafter. Notably, each of the plurality of targets extracted from existing data sources is associated with the pharmaceutical compound in at least one data record. It will be appreciated that the plurality of targets extracted from the existing data sources do not comprise known targets of the specified pharmaceutical compound.

Optionally, extracting the plurality of targets from the existing data sources further comprises identifying targets of pharmaceutical compounds similar to the specified pharmaceutical compound. It will be appreciated that the specified pharmaceutical compound may include similar pharmaceutical compounds available in the existing data sources. Additionally, such similar pharmaceutical compounds may possess characteristics closer to the specified pharmaceutical compound. Furthermore, on extraction of such similar pharmaceutical compounds, targets associated with the similar pharmaceutical compounds may also be identified. Additionally optionally, extracting the plurality of targets from the existing data sources further comprises identifying targets similar to the at least one known target. It may be evident that the existing data sources may include the information about targets similar to the at least one known target. Moreover, the existing data sources may be crawled to acquire similar targets exhibiting similar activities to the at least one known target.

The method of identifying potential targets for the pharmaceutical compound comprises analysing druggability of each of the plurality of targets to determine a preliminary set of targets. Furthermore, the processing module operable to analyse druggability of each of the plurality of targets to determine a preliminary set of targets. It will be appreciated that the term "druggability" of a target relates to an affinity of the target to bind with the pharmaceutical compound, altering the function of the target and providing a therapeutic benefit to a patient. Furthermore, the druggability of a target may be based on several parameters such as precedence based (whether a target belongs to an identified target family or not), structure based (whether a target possess is a well-recognized structure or not), activity based (whether activity of a target is well defined or not) and so forth. Therefore, the analysis of druggability of each of the plurality of targets is carried out to check whether each of the plurality of targets are druggable or not. Additionally, the druggability of each of the plurality of targets is determined to detect the affinity of a target towards a pharmaceutical compound. Furthermore, the druggability of each of the plurality of targets is analysed to determine a preliminary set of targets that are druggable and can be considered for further examinations, filtrations, and so forth.

The method of identifying potential targets for the pharmaceutical compound comprises determining a net score for each of the targets in the preliminary set of targets. The processing module is operable to determine a net score for each of the targets in the preliminary set of targets. It will be appreciated that the term 'net score' used herein relates to a predefined set of parameters to evaluate each of the targets in the preliminary set of targets. Furthermore, the net score provides an evaluation for each of the targets in the preliminary set of targets to determine the properties, characteristics, structures, co-relations and so forth. Additionally, the processing module is operable to evaluate each of the targets in the preliminary set of targets based on the predefined set of parameters.

Optionally, the method of identifying potential targets for the pharmaceutical compound comprises determining the net score for a target based on a genetic association score, wherein the genetic association score comprises likelihood of mutation in the target. More optionally, the processing module is operable to determine the net score for a target based on the genetic association score. It will be appreciated that the term "genetic association score" relates to observations of a change in genetic variants associated with a disease or trait. Furthermore, mutations in genetic variants may lead to disease or trait. In addition, mutations may include transformations, structural changes, behavioural changes and so forth. Specifically, the genetic association score of the target is based on the likelihood of mutations in the genetic variants of the target. More specifically, the processing module is operable to detect the genetic association score of the target based on the likelihood of mutations in the genetic variants of the target. Furthermore, a higher genetic association score signifies a higher likelihood of mutations in the target.

Optionally, the method of identifying potential targets for the pharmaceutical compound comprises determining the net score for a target based on a gene expression score, wherein the gene expression score is based on number of available gene expression studies related to the target. Optionally, the processing module is operable to determine the net score for a target based on a gene expression score. It will be appreciated that the term "gene expression score" relates to a count of expressed genes (well defined or discovered) in a target. Furthermore, the gene expression in a target defines the dominant or recessive of the genetic variants thereto. Additionally, higher number expressed genes in a target may result in better gene expression score of the target. Specifically, the gene expression score of the target is based on the count of expressed genes in the target. More specifically, the processing module is operable to detect the gene expression score of the target is based on the count of expressed genes in the target.

Optionally, the method of identifying potential targets for the pharmaceutical compound comprises determining the net score for a target based on a somatic association score, wherein the somatic association score comprises likelihood of somatic mutations in the target. Optionally, the processing module operable to determine the net score for a target based on the somatic association score. It will be appreciated that the term "somatic association score" relates to an account of probability of occurrence of somatic mutations (mutations in sexual hormones, ovule, sperms and so forth) in a target. Furthermore, somatic mutations are changes to the genetics of a target of a multicellular organism which are not passed on to offspring through germlines. In addition, mutations may include transformations, structural changes, behavioural changes and so forth.

Specifically, the somatic association score of the target is based on the likelihood of somatic mutations in the genetics of the target of the multicellular organism. More specifically, the processing module is operable to detect the somatic association score of the target based on the likelihood of somatic mutations in the genetics of the target.

Optionally, the method of identifying potential targets for the pharmaceutical compound comprises determining the net score for a target based on a pathway score, wherein the pathway score is based on a number of pathways related to the target. Optionally, the processing module is operable to determine the net score for a target based on the pathway score. It will be appreciated that the term 'pathway score' relates to a count of pathways associated with a target. Furthermore, the pathway is a series of interactions among molecules in a target that leads to a certain product or a change in a living organism. In addition, a higher pathway score may signify a higher number of pathways associated with target. Moreover, the processing module is operable to determine the pathway score of the target based on the count of pathways associated with the target.

Optionally, the method of identifying potential targets for the pharmaceutical compound comprises determining the net score for a target based on a gene ontology score, wherein the gene ontology score is based on number of available gene ontologies related to the target. Optionally, the processing module is operable to determine the net score for a target based on the gene ontology score. It will be appreciated that the term "gene ontology score" relates to an account of represented gene and gene product across all species. Furthermore, the gene ontology is a gene nomenclature that classifies and represents the genes and gene products. Additionally, targets with well classified and represented genes in the gene ontologies are provided with higher gene ontology scores. Moreover, the processing module is operable to determine the gene ontology score of the target based on count of represented gene and gene product of the target in gene ontologies.

Optionally, the net score of a target is further based on number of data-records associated with the target in the existing data sources. Specifically, each of the plurality of targets is identified from the existing data sources, wherein each of the plurality of targets is associated with the pharmaceutical compound in at least one data record. Therefore, the net score is further determined based on the number of data records associated with a target in the existing data sources. More specifically, a higher the number of data records comprising a target associated with the pharmaceutical compound may improve the net score of a target.

The method of identifying potential targets for the pharmaceutical compound comprises designating targets with the net score above a predefined threshold, as the potential targets. The processing module is operable to designate targets with the net score above the predefined threshold, as the potential targets. It will be appreciated that the term 'predefined threshold' relates to a minimal score, considered to be a reference value for a target to qualify as a potential target. Moreover, the targets above the predefined threshold are selected as the potential targets.

Optionally, the method of identifying potential targets for the pharmaceutical compound further comprises arranging the identified potential targets in a hypergeometric distribution based on the specified pharmaceutical compound. Optionally, the processing module is further operable to arrange the identified potential targets in a hypergeometric distribution based on the specified pharmaceutical compound. It will be appreciated that the term "hypergeometric distribution" relates to a sorting in an order of higher to lower and vice-versa. Furthermore, on the basis of net score, the potential targets are arranged in the hypergeometric distribution to classify the potential targets in higher order of potential.

Furthermore, there is disclosed a computer readable medium containing program instructions for execution on a computer system, which when executed by a computer, cause the computer to perform method steps for method of identifying potential targets for a pharmaceutical compound. The method comprises the steps of specifying the pharmaceutical compound, wherein the pharmaceutical compound is associated with at least one known target; extracting plurality of targets from existing data sources, wherein the existing data sources comprise plurality of data records and wherein each of the plurality of targets is associated with the pharmaceutical compound in at least one data record; analysing druggability of each of the plurality of targets to determine a preliminary set of targets; determining a net score for each of the targets in the preliminary set of targets; and designating targets with a net score above a predefined threshold, as the potential targets.

Optionally, the machine-readable non-transient data storage media comprises one of a floppy disk, a hard disk, a high capacity read only memory in the form of an optically read compact disk or CD-ROM, a DVD, a tape, a read only memory (ROM), and a random access memory (RAM).

DETAILED DESCRIPTION OF THE DRAWINGS

Referring to FIG. 1, illustrated are steps of a method 100 of identifying potential targets for a pharmaceutical compound, in accordance with an embodiment of the present disclosure. At a step 102, the pharmaceutical compound is specified. Moreover, the pharmaceutical compound is associated with at least one known target. At a step 104, plurality of targets is extracted from existing data sources. Furthermore, the existing data sources comprise plurality of data records. Additionally, each of the plurality of targets is associated with the pharmaceutical compound in at least one data record. At a step 106, druggability of each of the plurality of targets is analysed to determine a preliminary set of targets. At a step 108, a net score is determined for each of the targets in the preliminary set of targets. At a step 110, targets with a net score above a predefined threshold are designated as the potential targets.

Figure 2:
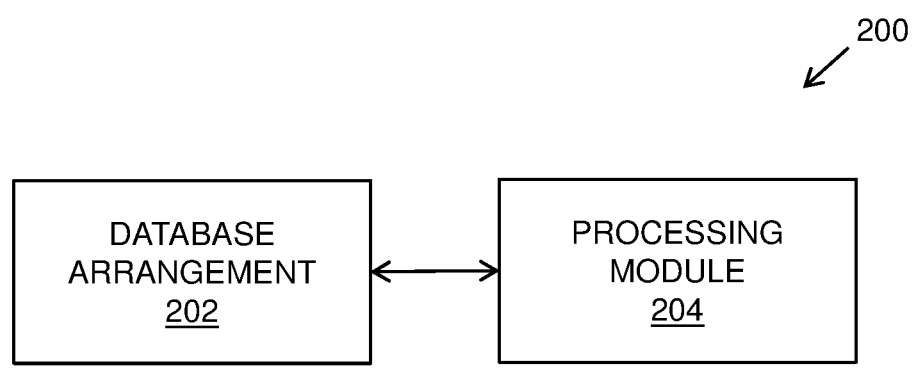
FIG. 2 is a block diagram of a system that identifies potential targets for a pharmaceutical compound, in accordance with an embodiment of the present disclosure.

Referring to FIG. 2, illustrated is a block diagram of a system 200 that identifies potential targets for a pharmaceutical compound, in accordance with an embodiment of the present disclosure. The system comprises a database arrangement 202 and a processing module 204 communicably coupled to the database arrangement. The database arrangement 202 is operable to store existing data sources and information related to the pharmaceutical compound. The processing module 204 operable to receive information related to the pharmaceutical compound, extract plurality of targets from existing data sources, analyse druggability of each of the plurality of targets to determine a preliminary set of targets, determine a net score for each of the targets in the preliminary set of targets, and designate targets with a net score above a predefined threshold, as the potential targets.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present. Reference to the singular is also to be construed to relate to the plural.

What is claimed is:

1. A system that identifies potential targets for a pharmaceutical compound, wherein the system includes a computer system, wherein the system comprises:
   a database arrangement operable to store existing data sources and information related to the pharmaceutical compound; and
   a processing module communicably coupled to the database arrangement, the processing module operable to:
      receive information related to the pharmaceutical compound, wherein the information comprises at least one known target associated with the pharmaceutical compound;
      extract plurality of targets from existing data sources, wherein the existing data sources comprises plurality of data records and wherein each of the plurality of targets is associated with the same pharmaceutical compound in each of the plurality of data records;
      analyse druggability of each of the plurality of targets to determine a preliminary set of targets;
      determine a net score for each of the targets in the preliminary set of targets; and
      identify targets with the net score above a predefined threshold, as the potential targets, wherein the potential targets correspond to unidentified sites of action for the pharmaceutical compound.

2. The system of claim 1, wherein the processing module is operable to determine the net score for a target in the preliminary set of targets, based on:
   a genetic association score, wherein the genetic association score comprises likelihood of mutation in the target;
   a gene expression score, wherein the gene expression score is based on number of available gene expression studies related to the target;
   a somatic association score, wherein the somatic association score comprises likelihood of somatic mutations in the target;
   a pathway score, wherein the pathway score is based on a number of pathways related to the target; and
   a gene ontology score, wherein the gene ontology score is based on number of available gene ontologies related to the target.

3. The system of claim 2, wherein the net score for the target is further based on number of data-records associated with the target in the existing data sources.

4. The system of claim 1, wherein the processing module is further operable to arrange the identified potential targets in a hypergeometric distribution based on the pharmaceutical compound.

5. The system of claim 1, wherein the extraction of the plurality of targets from the existing data sources further comprises:
   identification of targets of other pharmaceutical compounds similar to the pharmaceutical compound; and
   identification of targets similar to the at least one known target.

6. A method of identifying potential targets for a pharmaceutical compound, wherein the method includes using a computer system, wherein the method comprises:
   specifying the pharmaceutical compound, wherein the pharmaceutical compound is associated with at least one known target;
   extracting plurality of targets from existing data sources, wherein the existing data sources comprises plurality of data records and wherein each of the plurality of targets is associated with the same pharmaceutical compound in each of the plurality of data records;
   analysing druggability of each of the plurality of targets to determine a preliminary set of targets;
   determining a net score for each of the targets in the preliminary set of targets; and
   identifying targets with the net score above a predefined threshold, as the potential targets, wherein the potential targets correspond to unidentified sites of action for the pharmaceutical compound.

7. The method of claim 6, wherein the method comprises determining the net score for a target in the preliminary set of targets, based on:
   a genetic association score, wherein the genetic association score comprises likelihood of mutation in the target;
   a gene expression score, wherein the gene expression score is based on number of available gene expression studies related to the target;
   a somatic association score, wherein the somatic association score comprises likelihood of somatic mutations in the target;
   a pathway score, wherein the pathway score is based on a number of pathways related to the target; and
   a gene ontology score, wherein the gene ontology score is based on number of available gene ontologies related to the target.

8. The method of claim 7, wherein the net score for the target is further based on number of data-records associated with the target in the existing data sources.

9. The method of claim 6, wherein the method further comprises arranging the identified potential targets in a hypergeometric distribution based on the specified pharmaceutical compound.

10. The method of claim 6, wherein extracting the plurality of targets from existing data sources further comprises:
    identifying targets of other pharmaceutical compounds similar to the specified pharmaceutical compound; and
    identifying targets similar to the at least one known target.

11. A non-transitory computer readable medium, containing program instructions for execution on a computer system, which when executed by a computer, cause the computer to perform method steps for method of identifying potential targets for a pharmaceutical compound, the method comprising the steps of:

specifying the pharmaceutical compound, wherein the pharmaceutical compound is associated with at least one known target;

extracting plurality of targets from existing data sources, wherein the existing data sources comprises plurality of data records and wherein each of the plurality of targets is associated with the same pharmaceutical compound in each of the plurality of data records;

analysing druggability of each of the plurality of targets to determine a preliminary set of targets;

determining a net score for each of the targets in the preliminary set of targets; and identifying targets with the net score above a predefined threshold, as the potential targets, wherein the potential targets correspond to unidentified sites of action for the pharmaceutical compound.

\* \* \* \* \*